United States Patent
Tsubouchi

(10) Patent No.: US 11,291,436 B2
(45) Date of Patent: Apr. 5, 2022

(54) MITRAL VALVE RETRACTOR WITH SIDE MALLEABLE RETRACT FEATURE AND UNIVERSAL ADJUSTER

(71) Applicant: Terumo Cardiovascular Systems Corporation, Ann Arbor, MI (US)

(72) Inventor: Takeshi Tsubouchi, Dexter, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 266 days.

(21) Appl. No.: 16/582,105

(22) Filed: Sep. 25, 2019

(65) Prior Publication Data

US 2020/0015799 A1      Jan. 16, 2020

Related U.S. Application Data

(63) Continuation of application No. PCT/US2018/024733, filed on Mar. 28, 2018.

(60) Provisional application No. 62/477,470, filed on Mar. 28, 2017.

(51) Int. Cl.
*A61B 17/02* (2006.01)
*A61B 17/00* (2006.01)

(52) U.S. Cl.
CPC .............. *A61B 17/0206* (2013.01); *A61B 2017/00946* (2013.01); *A61B 2017/0237* (2013.01)

(58) Field of Classification Search
CPC ...... A61B 17/0206; A61B 2017/00946; A61B 2017/0237
USPC ................................. 600/201–245
See application file for complete search history.

(56) References Cited

U.S. PATENT DOCUMENTS

| | | | |
|---|---|---|---|
| 3,227,156 A * | 1/1966 | Gauthier | A61B 17/0293 600/231 |
| 3,463,144 A | 8/1969 | Hammond | |
| 4,048,987 A | 9/1977 | Hurson | |
| 4,337,762 A * | 7/1982 | Gauthier | A61B 17/0293 600/233 |
| 5,052,374 A | 10/1991 | Alvarez-Jacinto | |
| 5,875,782 A * | 3/1999 | Ferrari | A61B 17/0206 128/898 |
| 6,309,349 B1 * | 10/2001 | Bertolero | A61B 1/313 600/210 |
| 6,464,634 B1 | 10/2002 | Fraser | |
| 2004/0193018 A1 * | 9/2004 | Thalgott | A61B 17/02 600/227 |

(Continued)

OTHER PUBLICATIONS

PCT Written Opinion of International Searching Authority, PCT/US18/24733, dated May 10, 2018.

*Primary Examiner* — Eduardo C Robert
*Assistant Examiner* — Tara Rose E Carter
(74) *Attorney, Agent, or Firm* — Darryl Newell; MacMillan, Sobanski & Todd, LLC

(57) ABSTRACT

A retraction apparatus increases flexibility of retracting tissues around a surgical site, such as during cardiac surgery including mitral valve repair or other surgical procedures. A holder is configured to mount to a fixed rail such as a sternal retractor. A rake element comprises a strap segment having a proximal end slidably received in a slot in the holder. The rake element has a primary rake finger at a distal end of the strap segment configured to grasp and retract tissue at a surgical site and a sub-finger extending perpendicularly via a bendable wing from a side of the primary rake finger adapted to retract adjacent tissue around the surgical site.

10 Claims, 12 Drawing Sheets

(56) References Cited

U.S. PATENT DOCUMENTS

| | | | |
|---|---|---|---|
| 2006/0052671 A1 | 3/2006 | McCarthy | |
| 2007/0270654 A1 | 11/2007 | Pignato | |
| 2012/0271120 A1* | 10/2012 | Seex | A61B 17/02 600/235 |
| 2013/0245384 A1* | 9/2013 | Friedrich | A61B 90/50 600/230 |
| 2017/0065268 A1* | 3/2017 | Sindram | A61B 17/0206 |

* cited by examiner

MITRAL VALVE RETRACTOR WITH SIDE MALLEABLE RETRACT FEATURE AND UNIVERSAL ADJUSTER

CROSS REFERENCE TO RELATED APPLICATIONS

This application is a continuation of PCT Application No. PCT/US2018/024733, filed Mar. 28, 2018, based on and claiming priority to U.S. Provisional Application No. 62/477,470, filed Mar. 28, 2017, both of which are incorporated herein by reference in their entirety.

STATEMENT REGARDING FEDERALLY SPONSORED RESEARCH

Not Applicable.

BACKGROUND OF THE INVENTION

The invention applies to heart surgery, especially heart valve repair or replacement such as the repair of a mitral valve. In the case of a damaged valve, surgery is typically conducted to replace or repair the valve through an incision. For this operation, operating room assistant personnel may use a valve rake to keep a valve region round and stable for suturing.

Besides manually holding the valve rake, fixed mechanisms have been used to suspend a rake in a desired position. During cardiac surgery, a sternal retractor is typically mounted over the patient carrying retractor blades to separate overlying tissues to allow access to a surgical site. The frame of the sternal retractor has been used to support mechanical rakes, as in U.S. Pat. No. 5,772,583, for example.

To avoid complicated position adjustment mechanisms, it is also known to employ a flexible shaft for carrying the valve rakes. However, manipulation to obtain the desired position may require significant skill and may be inconvenient and time consuming. Furthermore, the size, thickness, and length requirements for flexible structures that can also provide sufficient stability for the desired holding characteristics has also resulted in large mechanisms that consume needed space within the surgical area, especially since several valve rakes may be needed simultaneously. Thus, it is desirable to provide adjustment mechanisms that are small and robust while being easy to adjust to a desired position and lock into place with minimal effort.

Due to limited space at a surgical site, only a limited number of retraction devices can be used at the same time. The width or a retraction finger or rake must be small enough to permit insertion into an incision. When the retraction finger tugs at a side of the incision opening, it usually creates a triangular-shaped space in the overlying tissue layer(s). Even after retraction using the known retraction fingers to visualize a mitral valve during mitral valve repair, for example, the anterolateral commissure and the posterolateral commissure may still be obscured by muscle tension or fatty tissue. It would be desirable to increase visualization without increasing the number of stabilizer arms being used.

SUMMARY OF THE INVENTION

The invention provides fast, simple, and secure adjustment in a compact design that maintains available space for surgical access while enabling a user to finely control a universal position adjustment which can be locked using a single knob. It also provides a rake structure that includes a malleable sub-finger extending from a side of a main retraction finger to extend the retraction force onto tissues disposed to the side of the main finger.

In one aspect of the invention, a retraction apparatus for surgical procedures comprises a holder configured to mount to a fixed rail of a sternal retractor. A held rake element comprises a strap segment having a proximal end slidably received in a slot in the holder. The rake element has a primary rake finger at a distal end of the strap segment configured to grasp and retract tissue at a surgical site and a sub-finger extending perpendicularly via a bendable wing from a side of the primary rake finger adapted to retract adjacent tissue around the surgical site.

DETAILED DESCRIPTION OF PREFERRED EMBODIMENTS

Figure 1:
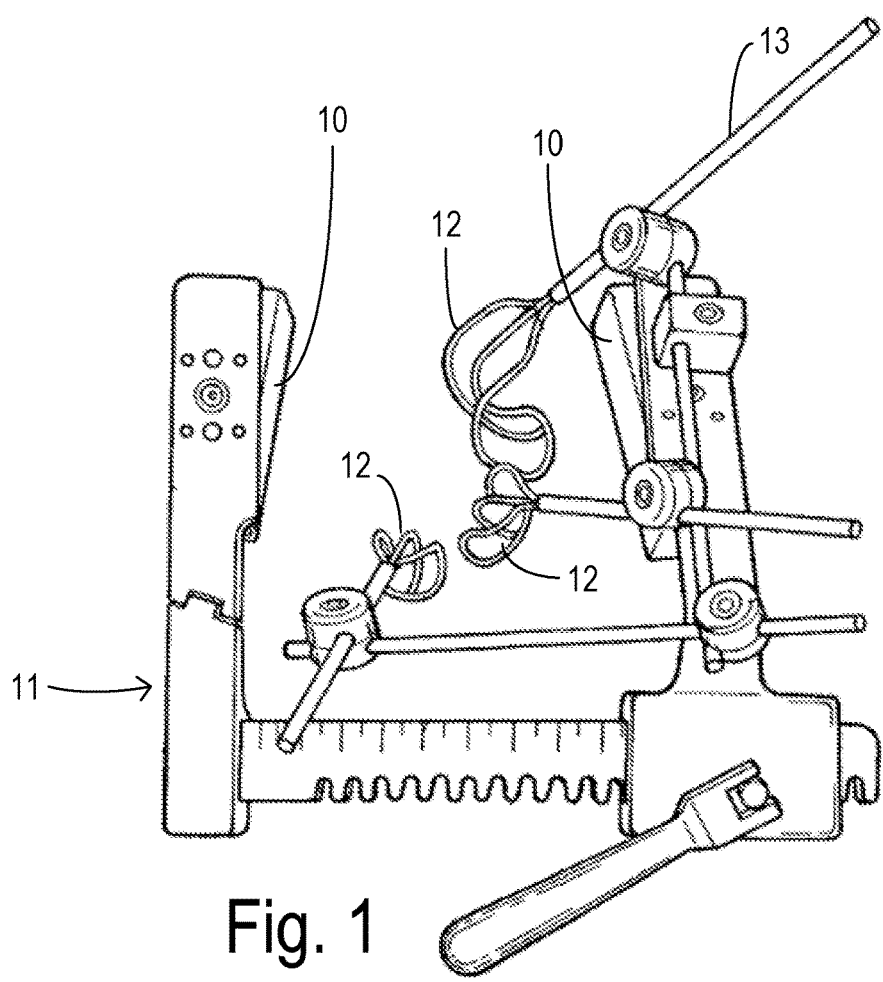
FIG. 1 is a top view of one example of a conventional sternal retractor system.
Figure 2:
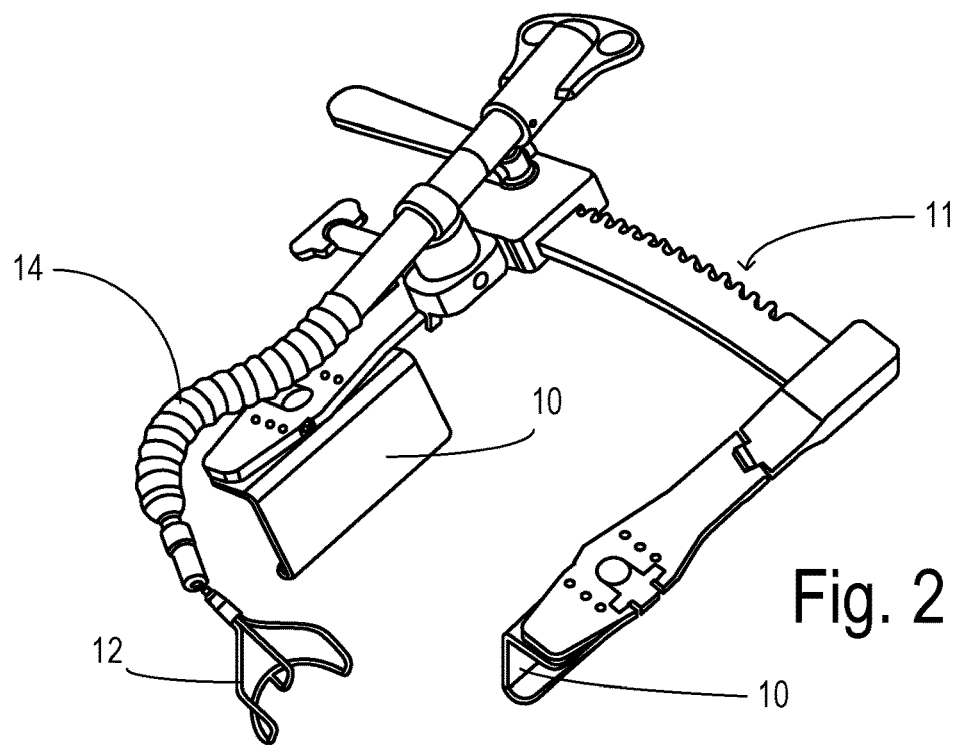
FIG. 2 is a perspective view of another example of a conventional sternal retractor system.

FIGS. 1 and 2 show prior art sternal retractors with spaced blades 10 carried by an adjustable frame 11. Valve rakes 12 are carried by rigid rods 13 or bendable rod 14, respectively. Each may have an adjustable suspension mechanism.

Figure 3:
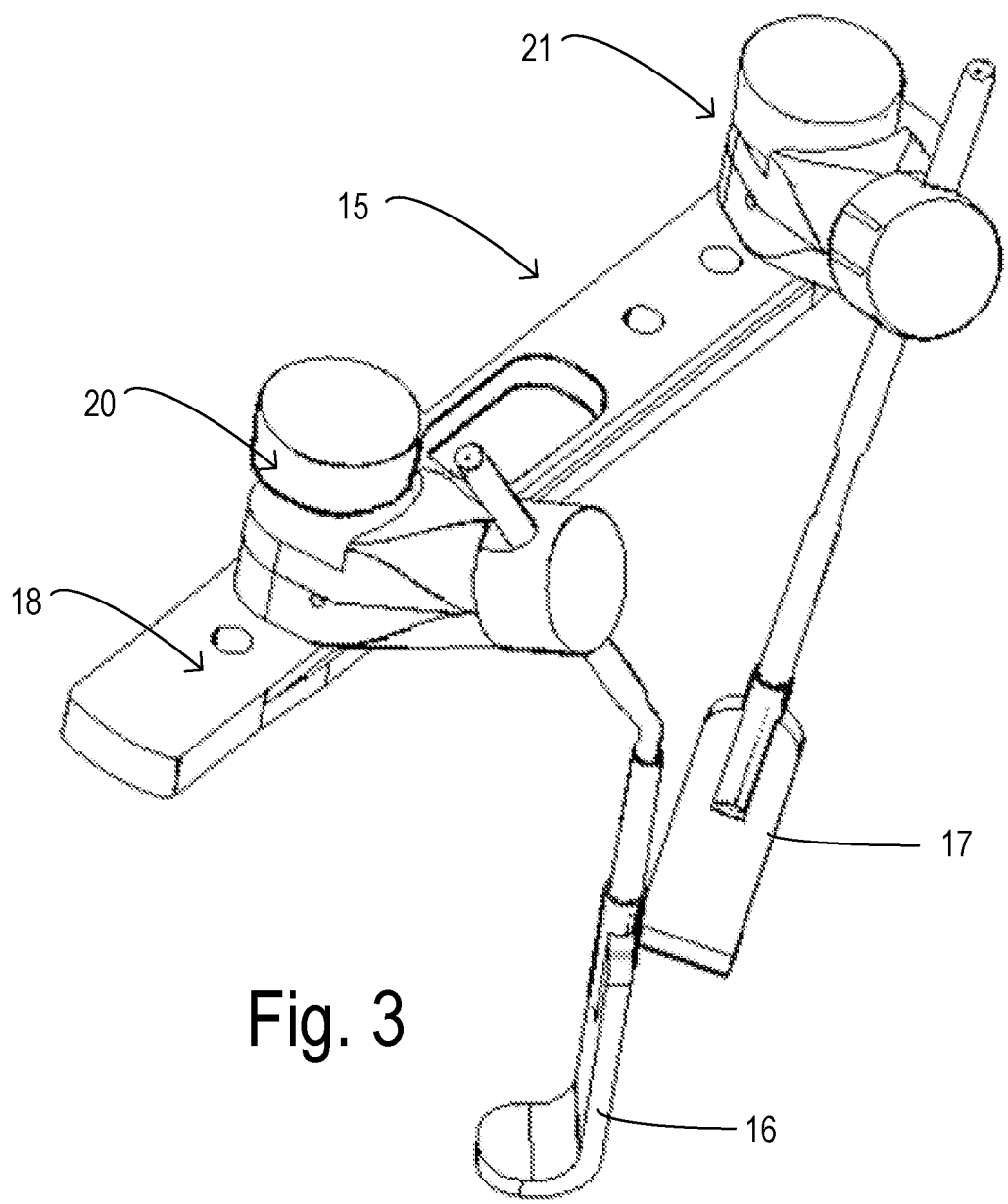
FIG. 3 is a perspective view of a retractor rake mounting system according to another example.

FIG. 3 shows another support system for cardiac valve retractors as disclosed in U.S. Patent Application Publication 2018/0042595 A1, published Feb. 15, 2018, entitled "Valve Rake and Mount for Surgical Retractor," which is incorporated herein by reference. Retractor rake fingers 16 and 17 are attached to a retractor slide 18 by mounting mechanisms 20 and 21, respectively, which are constructed as identical articulating joints.

Figure 4:
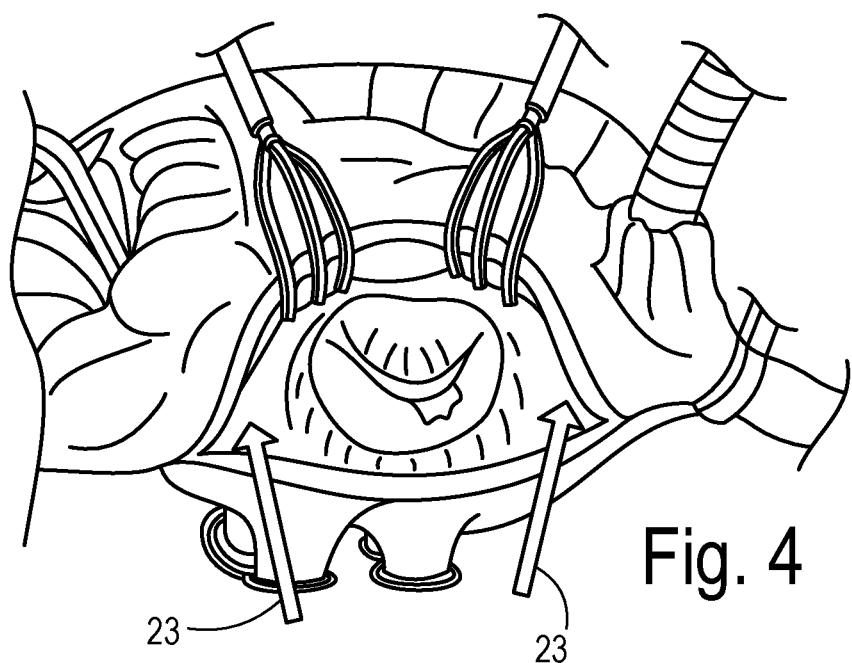
FIG. 4 is a diagram showing a mitral valve repair procedure.
Figure 5:
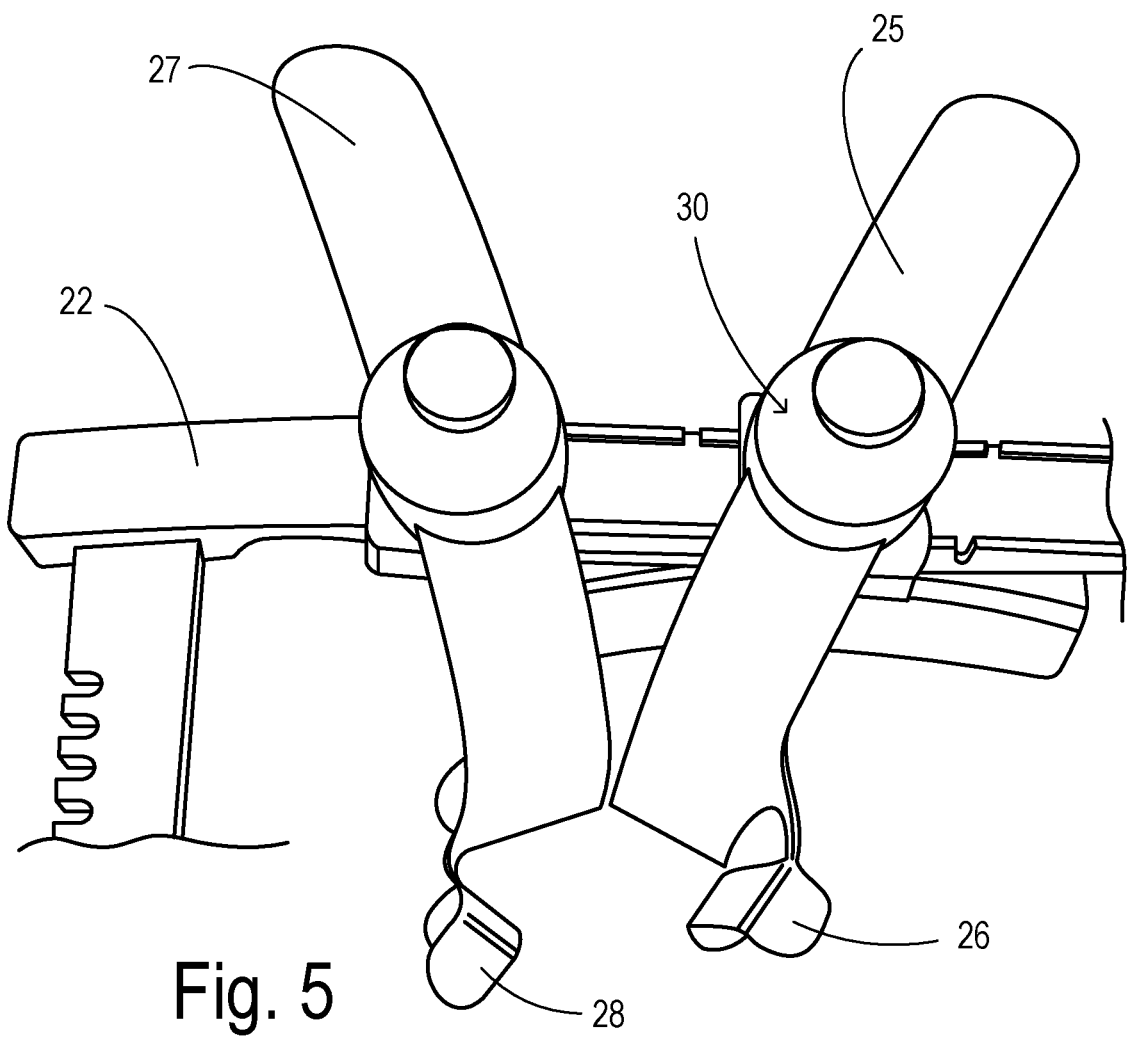
FIG. 5 is a to view of a pair of retractor units of one embodiment of the present invention mounted to a sternal retractor rail.
Figure 6:
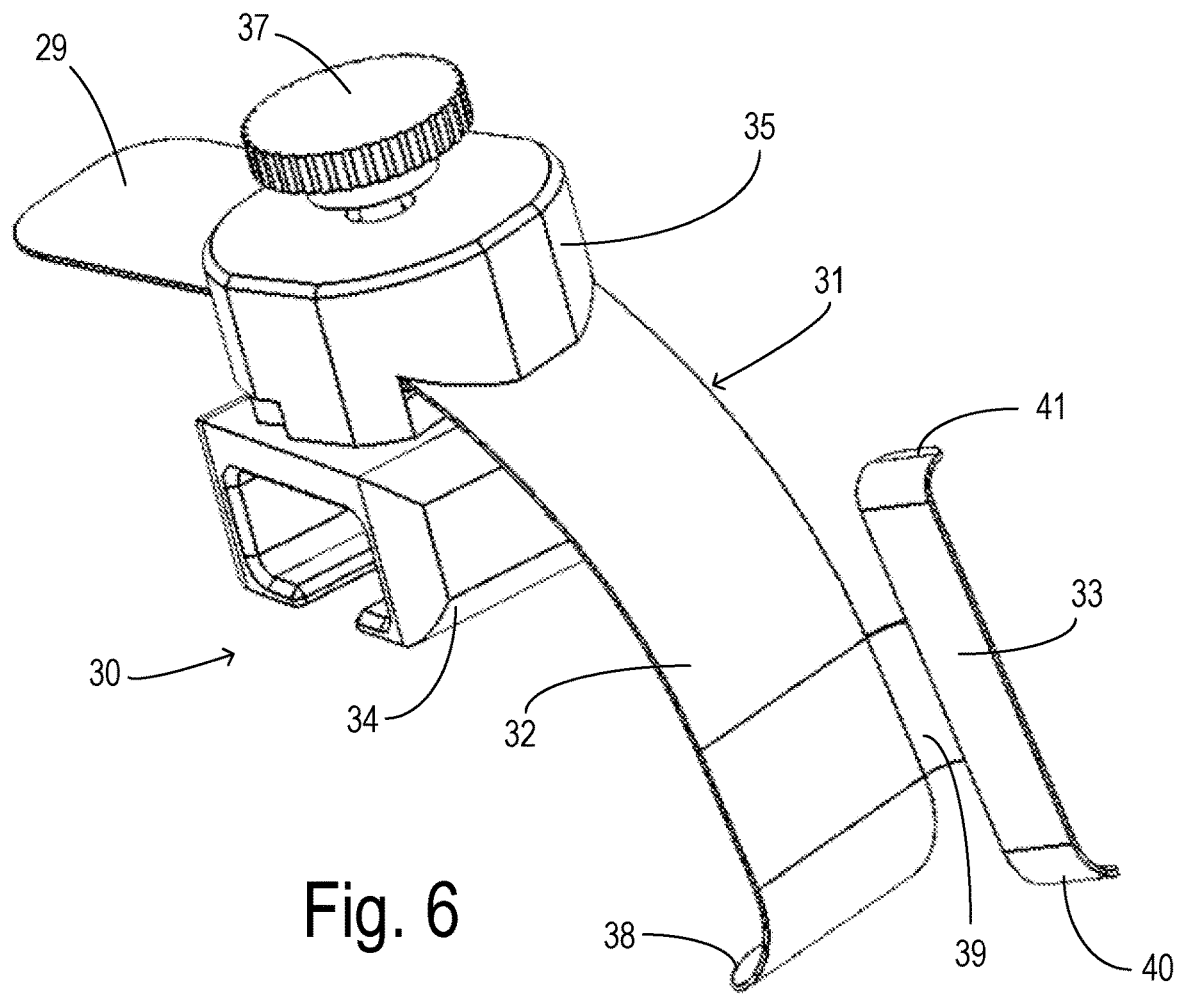
FIGS. 6 and 7 are perspective views of a retractor unit of FIG. 5.
Figure 7:
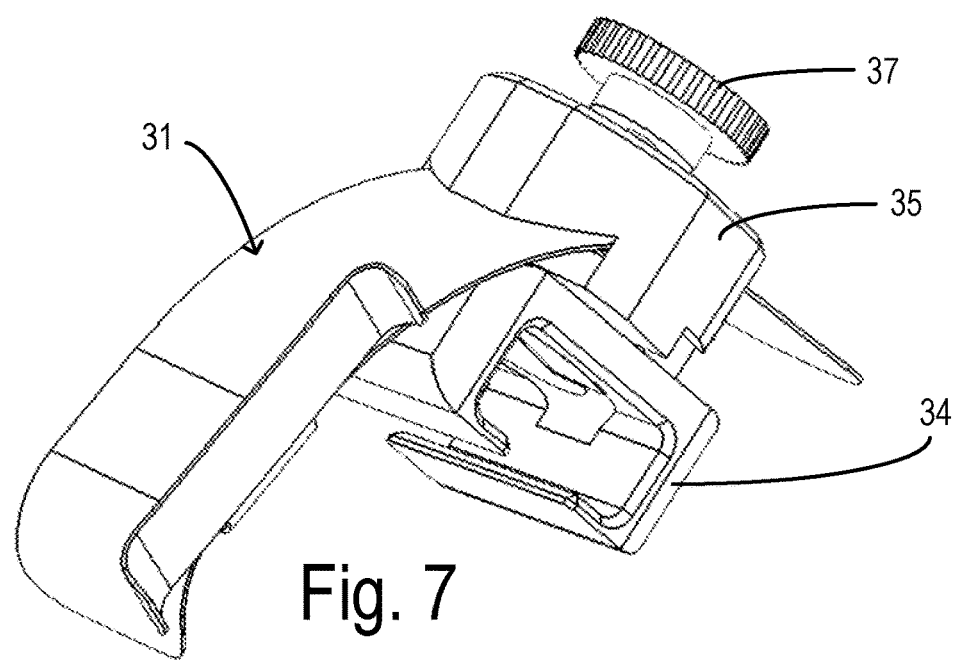
Figure 8:
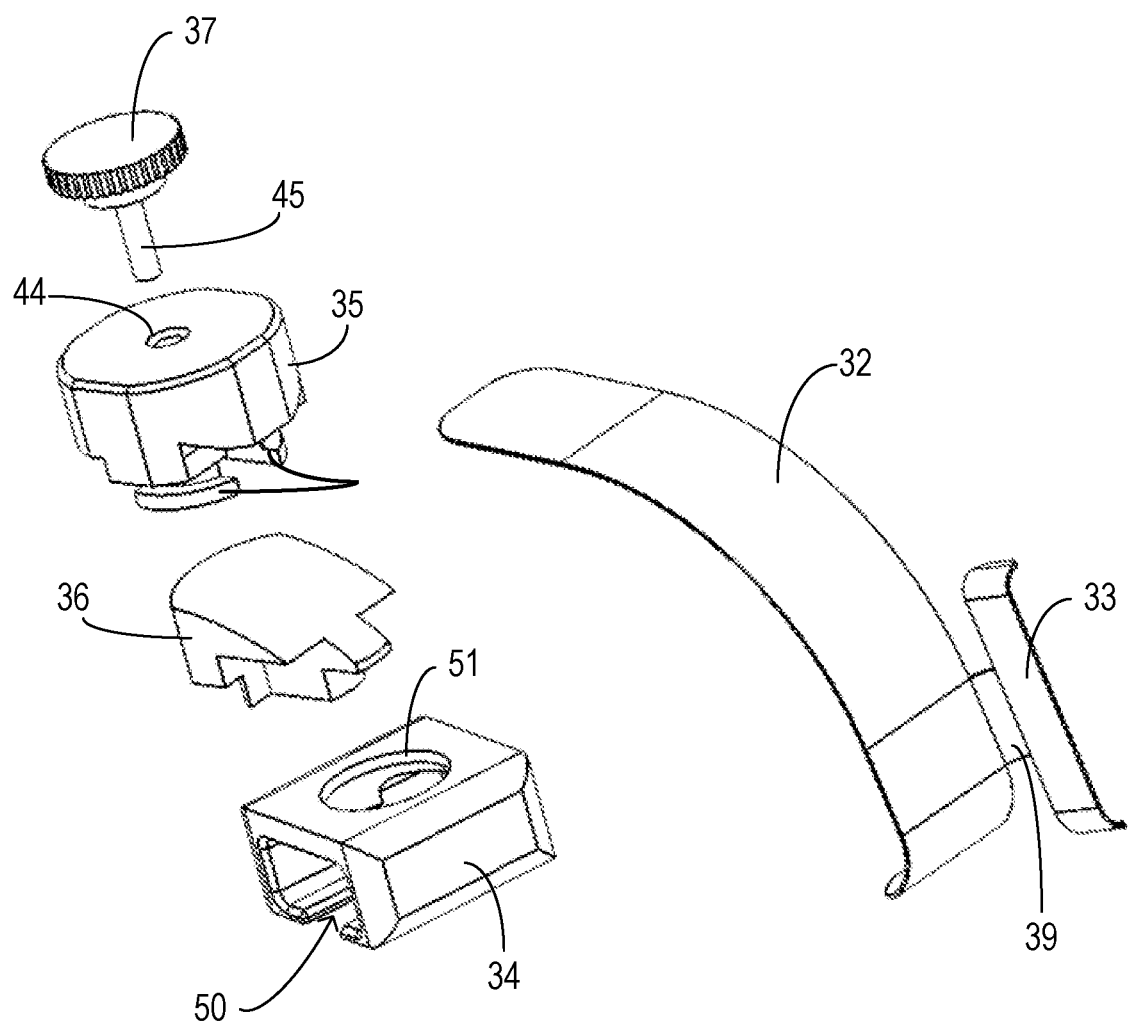
FIG. 8 is an exploded view of the retractor unit of FIG. 6.
Figure 9:
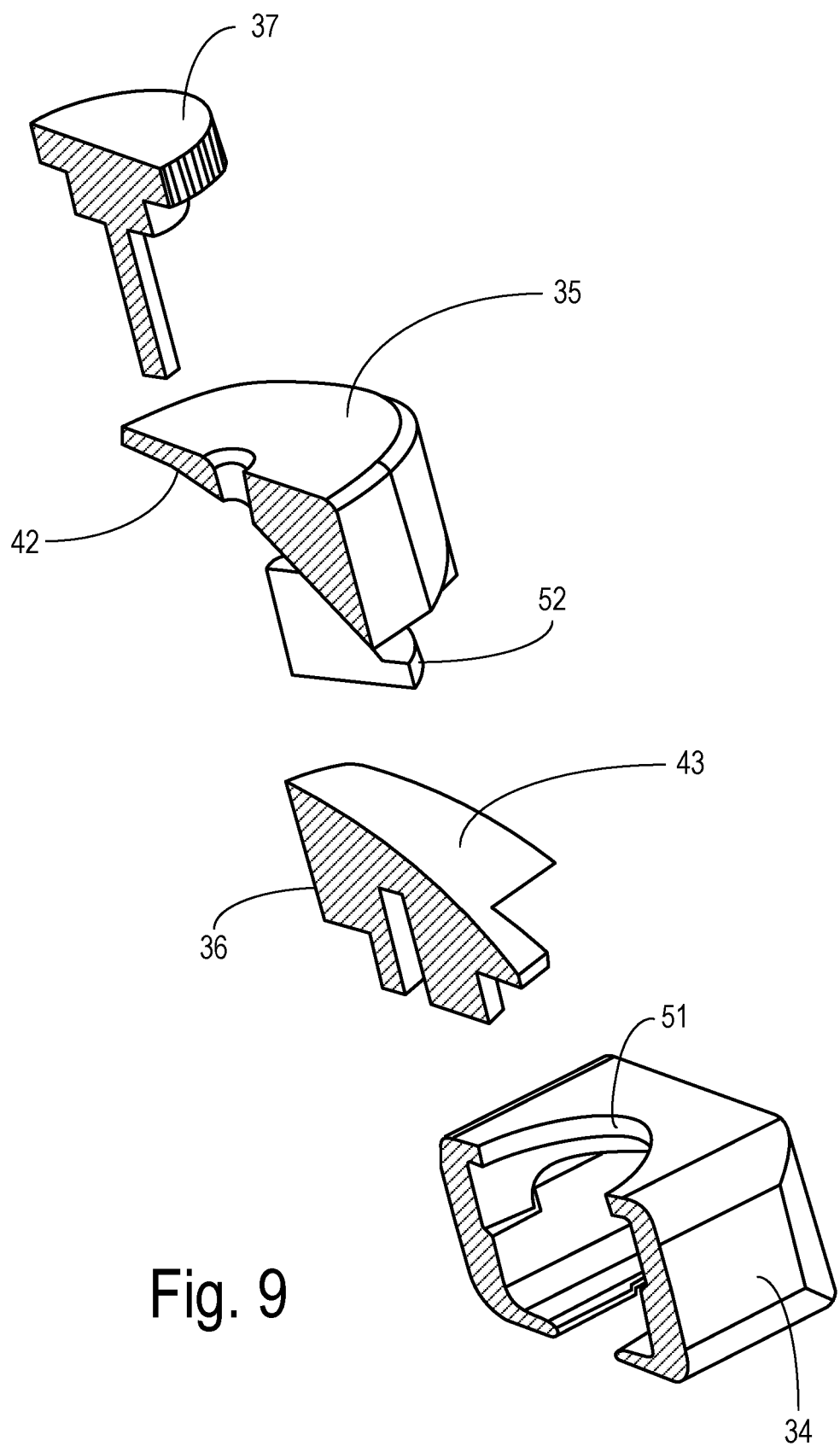
FIG. 9 is a cross-sectional, exploded view of some components of the retractor unit of FIG. 6.
Figure 10:
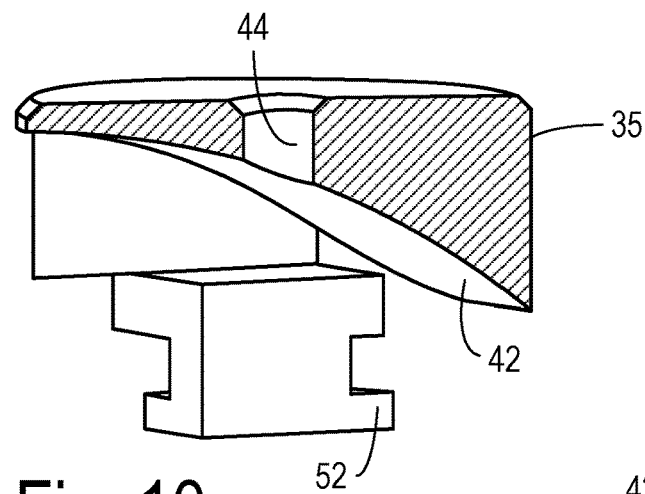
FIG. 10 is a cross-sectional view of the carriage block.

FIG. 4 shows a mitral valve repair procedure wherein a pair of retractor rakes are used to pull open an incision. A pair of arrows 23 indicate areas where an anterolateral commissure and a posteromedial commissure may potentially be obscured by muscle and/or fat. It is desired to expose these areas to perform the mitral valve repair. To increase the exposure of underlying tissue, one embodiment of the invention utilizes a rake structure as shown in FIG. 5 wherein a plate-shaped retractor member has a main finger 25 with an attached sub-finger 26 extending from one of its sides in order to engage tissue to the side of main finger 25. Finger 25 and sub-finger 26 are preferably formed of a malleable metal having sufficient flexibility to allow shaping as desired and having sufficient retention strength to retract the tissues as desired. Any biocompatible metal or metal alloy can be used (e.g., stainless steel, titanium, or nickel-titanium), as well as resilient plastic material and composite or coated bodies. Finger 25 is mounted by a holder 30 to a fixed retractor rail 22. Holder 30 has an articulating mechanism which provides universal adjustment for the positioning of finger 25 by allowing rotation of holder 30 and longitudinal sliding of finger 25 radially from holder 30 when holder 30 is in an unlocked condition. Since finger 25 and sub-finger 26 are formed of malleable material, their positions and shapes are independently adjustable. Preferably, two (or more) of retractors and their respective holders may be provided on rail 22 with their sub-fingers. A sub-finger can extend from the other side of the main fingers as shown by finger 27 and sub-finger 28. Sub-fingers could also extend on both sides of a sub-finger.

This first embodiment of a retraction apparatus is shown in greater detail in FIGS. 6-15 having holder 30 and a rake element 31. Rake element 31 is formed by a thin metal sheet or plate to provide a strap segment 29 at a proximal end (retained in holder 30) leading to a main finger 32 and a sub-finger 33 at the distal end. Strap segment 29 is anchored to a traveler member 34 by a carriage block 35, a wedge piece 36, and a screw knob or tightener 37. Main finger 32 is slidable through an angled slot between carriage block 35 and wedge piece 36. Finger 32 has a hook-shaped distal end 38 for grasping the tissue being retracted. A side wing 39 attaches sub-finger 33 to finger 32. Sub-finger 33 is comprised of a strip extending generally perpendicular to finger 32 and having hooked ends 40 and 41. Hooked distal end 40 is adapted to grasp additional tissues being retracted, and hooked end 41 provides a manual grasping feature to facilitate manual bending of sub-finger 33 and wing 39 into a desired configuration. Side wing 39 has a width sufficient to permit a desired bending radius, but it extends along a limited portion of the side of sub-finger 33 for ease of manipulation and to allow some multi-axis twisting.

Figure 11:
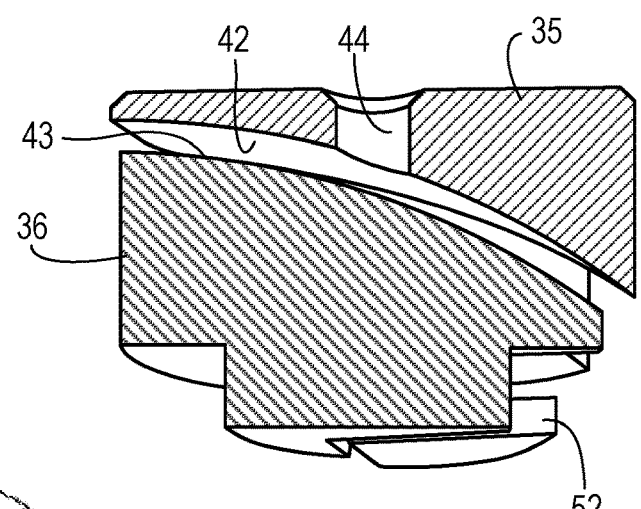
FIG. 11 is a cross-sectional view of the carriage block and the wedge piece.
Figure 12:
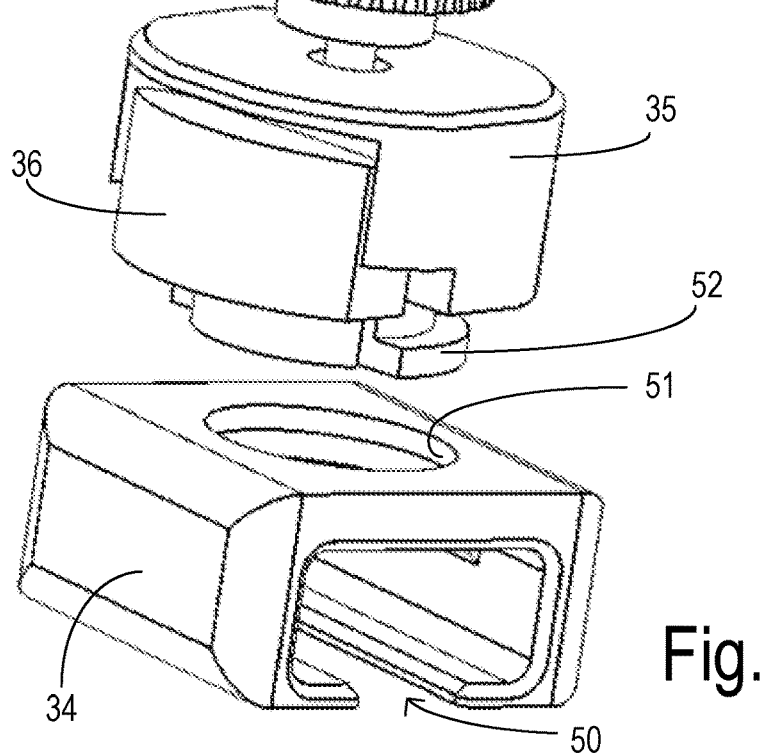
FIG. 12 is a partially exploded, perspective view of some components of the retractor unit of FIG. 6.
Figure 13:
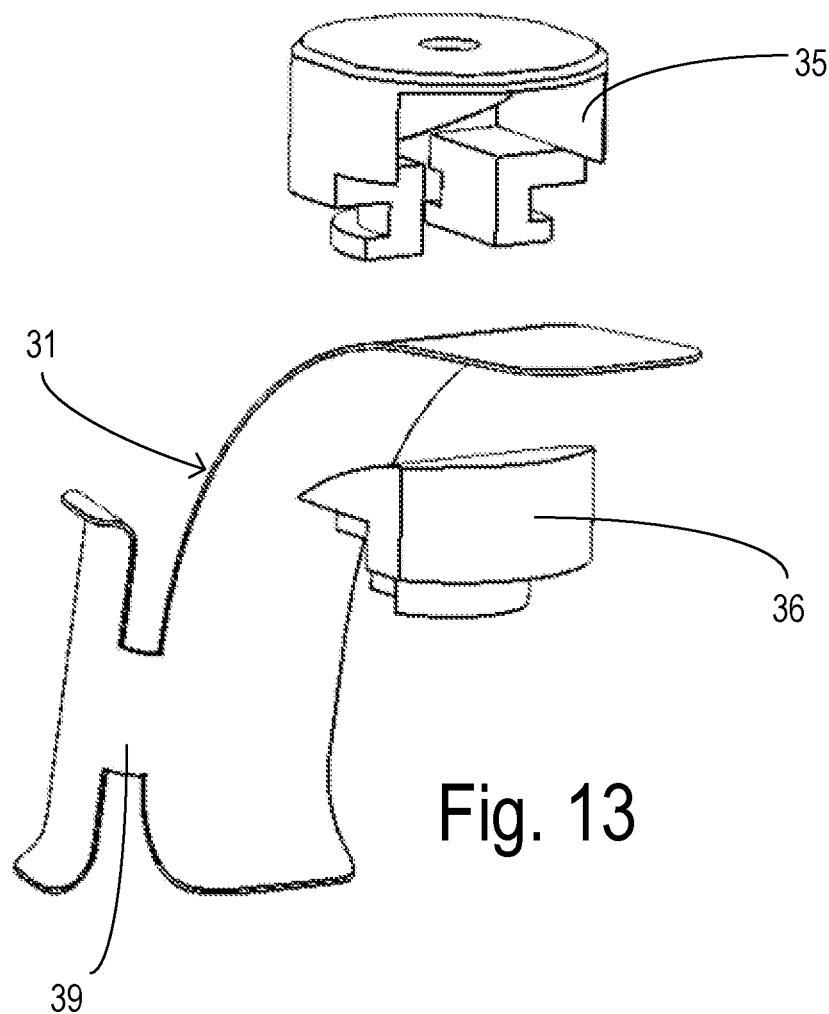
FIG. 13 is a partially exploded, perspective view of some other components of the retractor unit of FIG. 6.

To facilitate sliding of finger 32 in a direction generally towards and away from the surgical site, the slot between carriage block 35 and wedge piece 36 is slanted and curves downward as defined by a sloping surface 42 on carriage block 35 and a sloping surface 43 on wedge piece 36. FIG. 11 shows the curving slot between surfaces 42 and 43 that receives finger 32. Carriage block 35 has a threaded aperture passing through surface 42 which receives a threaded shaft 45 of screw knob 37. To lock finger 32 at a desired position, screw knob 37 is turned so that shaft 45 advances through aperture 44 to push against finger 32, thereby clamping the articulating mechanism and strap segment 29 so that primary rake finger 32 and sub-finger 33 are extended to a desired location for retracting the tissue.

Figure 14:
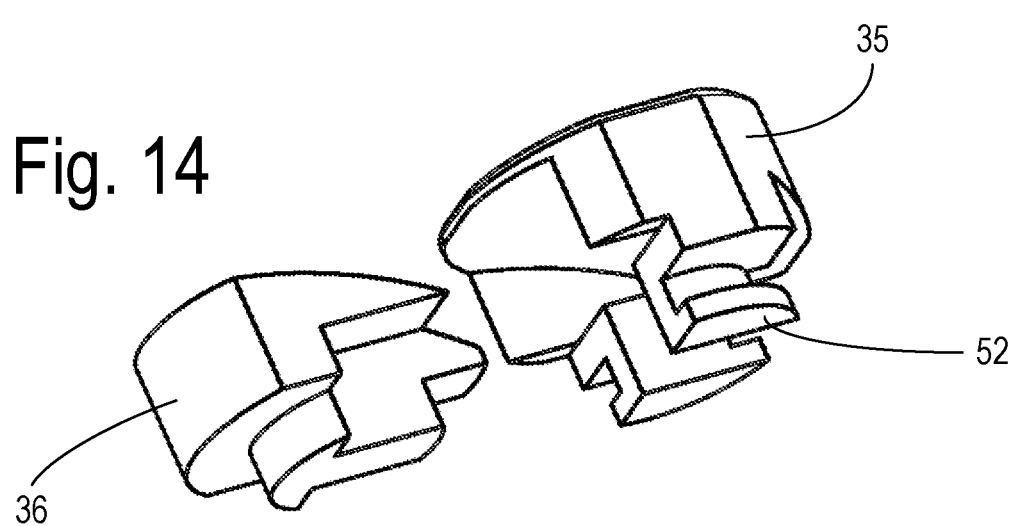
FIG. 14 is a perspective view of the carriage block and wedge piece showing the manner in which the wedge piece is inserted into the carriage block.
Figure 15:
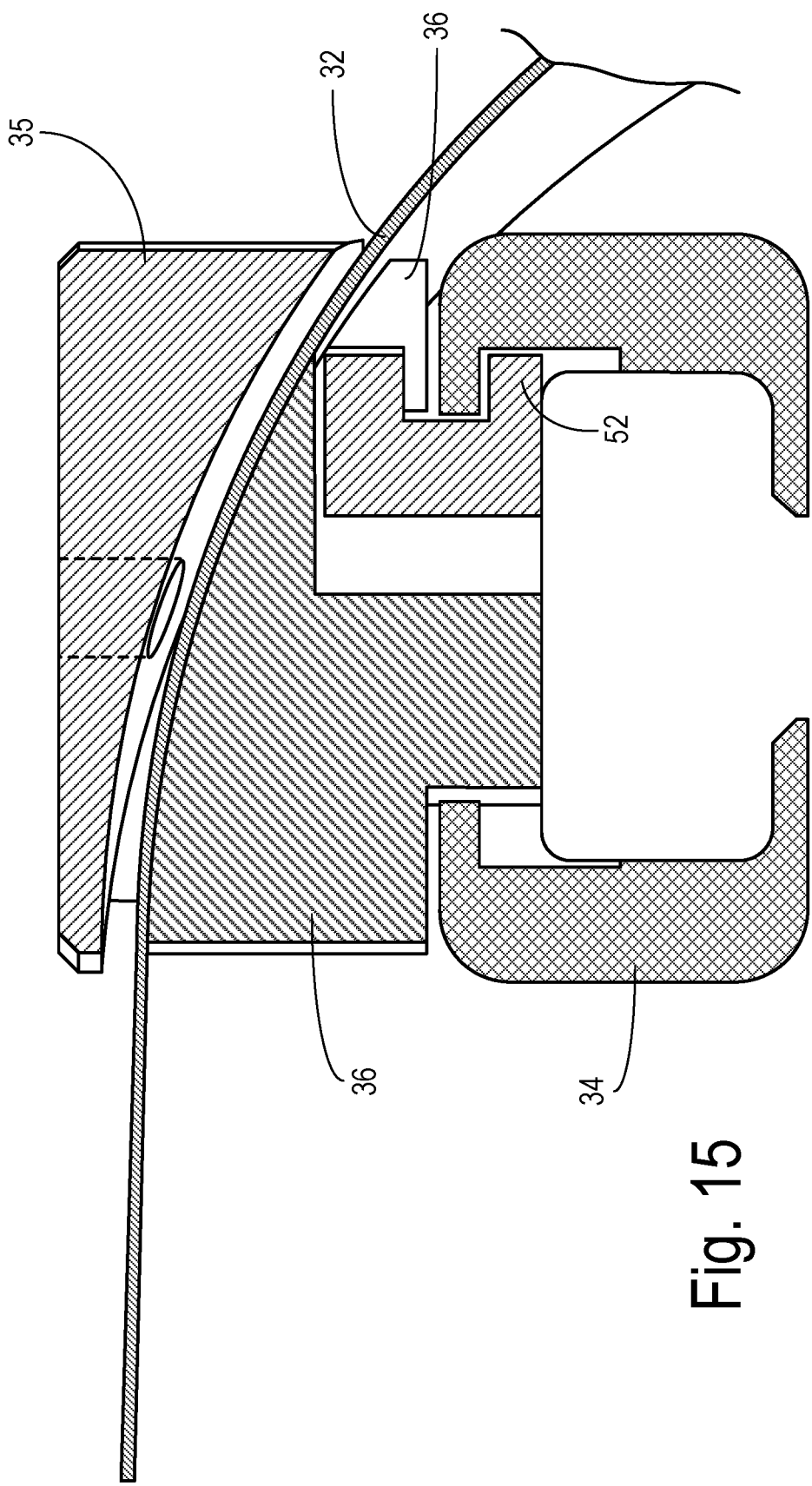
FIG. 15 is a cross section showing the strap segment passing through the slot of the retractor unit of FIG. 6.
Figure 16:
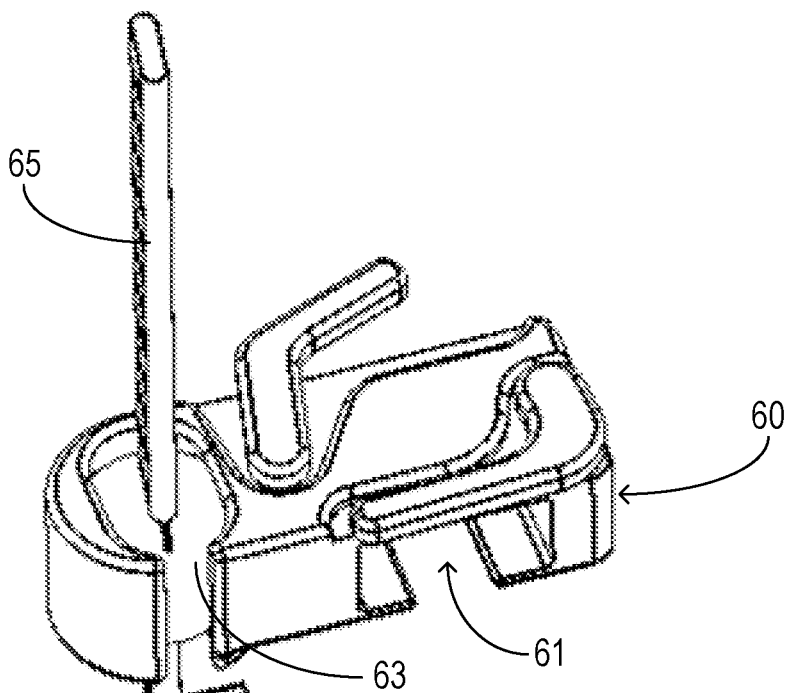
FIGS. 16 and 17 are perspective views of another embodiment of a retractor unit of the invention.
Figure 16:
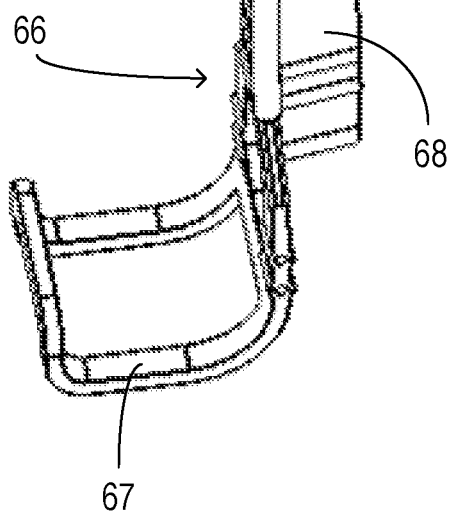
Figure 17:
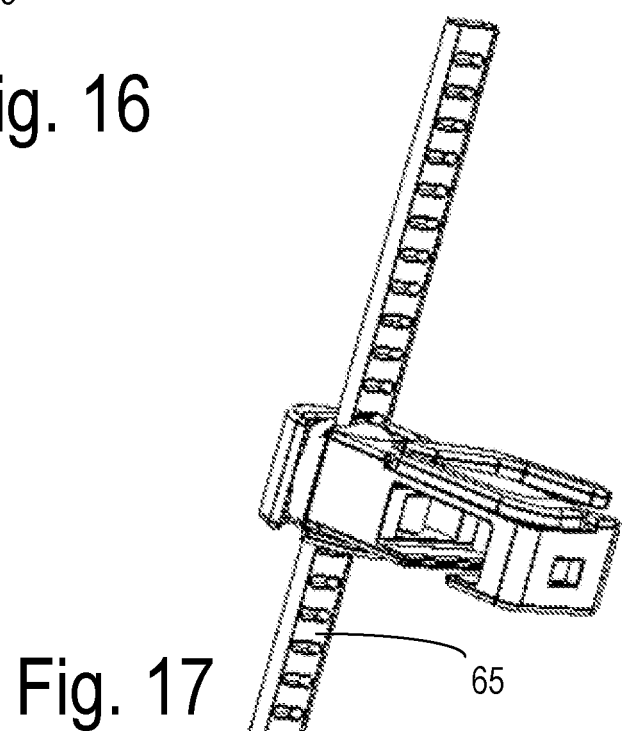
Figure 18:
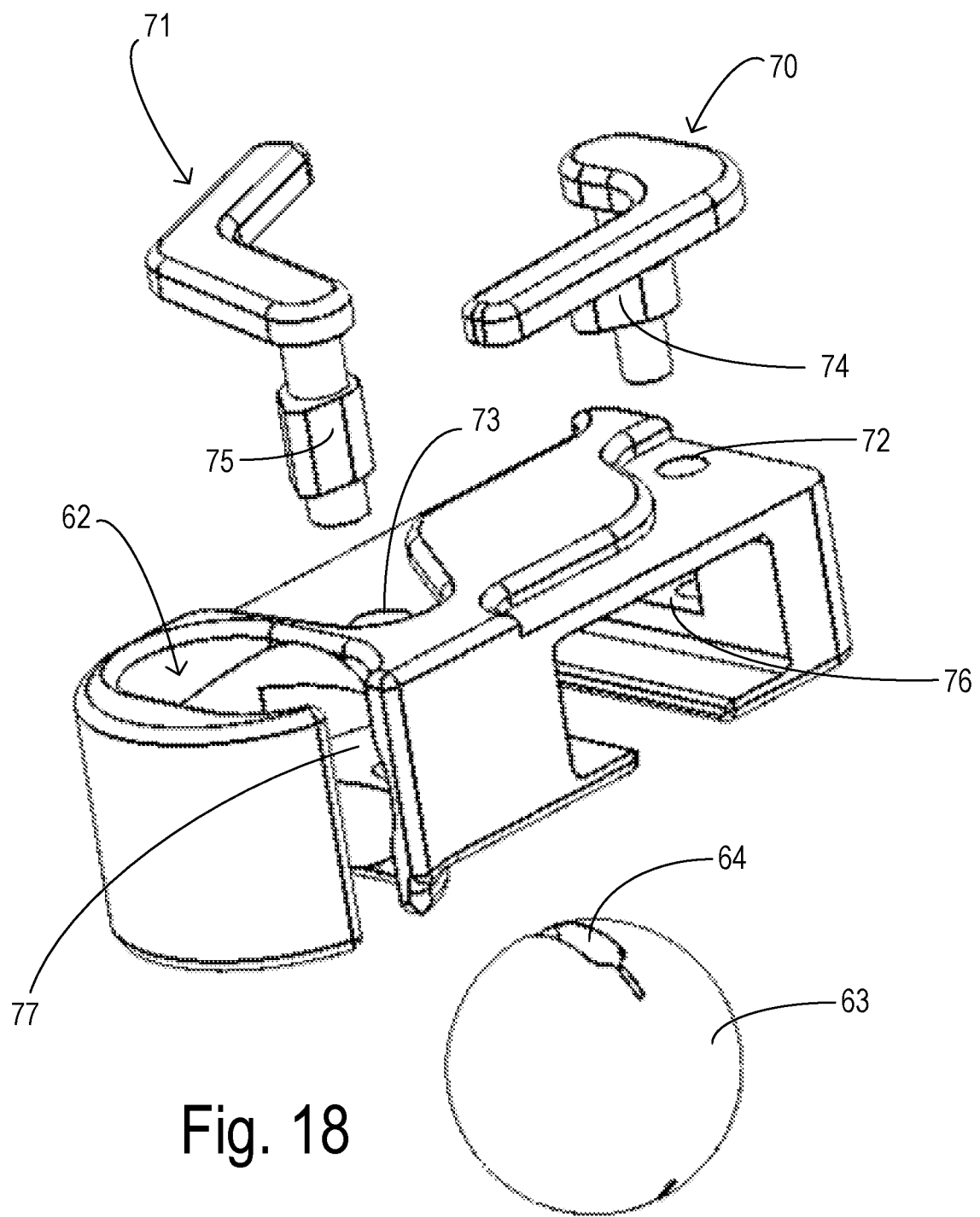
FIG. 18 is an exploded, partial view of the retractor unit of FIG. 16.
Figure 19:
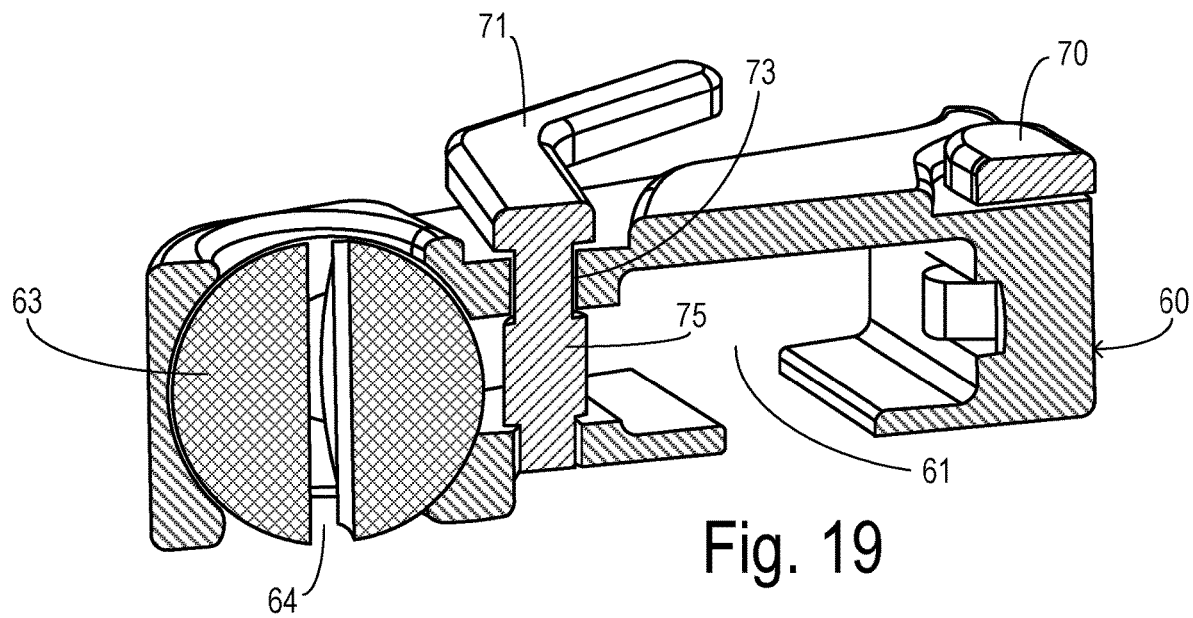
FIG. 19 is a cross section of some components of the retractor unit of FIG. 16.
Figure 20:
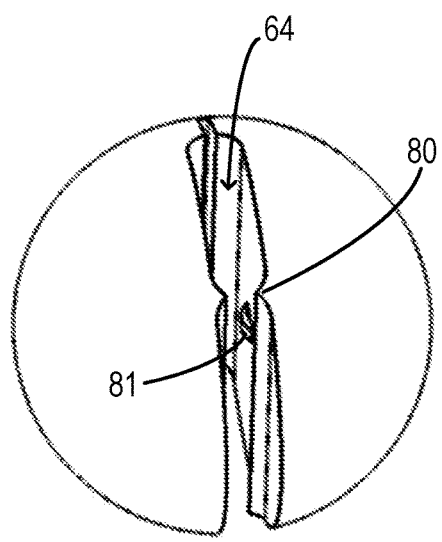
FIG. 20 is a perspective view of the compressible ball of the retractor unit of FIG. 16.
Figure 21:
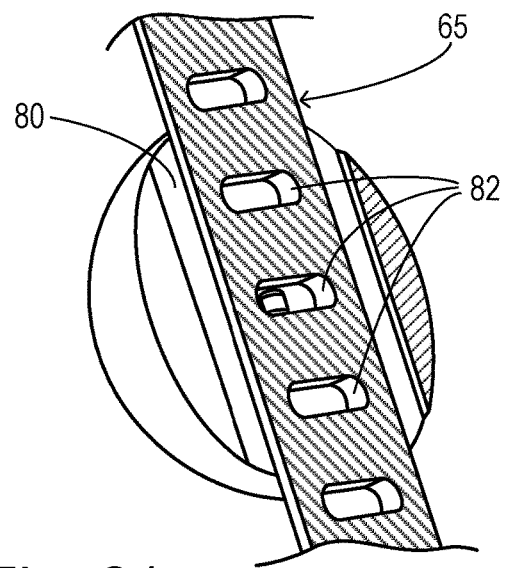
FIG. 21 is a cross-sectional, perspective view of the compressible ball and strap segment of the retractor unit of FIG. 16.

Traveler 34 has an internal passageway 50 to receive the fixed rail of the sternal retractor. A top hole 51 in carriage block 35 is round and receives a round axle portion formed by lower extensions on carriage block 35 and wedge piece 36 so that the holder can rotate within hole 51. Carriage block 35 has a pair of flanges 52 that reside within passageway 50 to capture an edge of hole 51. When screw knob 37 is tightened, an upward movement of carriage block 35 (see FIG. 15) as shaft 45 presses against strap segment 29 is limited by flanges 52 and further tightening of screw knob 37 presses portions of wedge piece 36 against an upper surface of retractor rail 22 and against an inner surface of top hole 51. Thus, the holder becomes locked (i.e., finger 32 can no longer move within the slot, carriage block 35 and wedge piece 36 are prevented from rotating, and traveler 34 is prevented from moving along the rail). FIG. 14 shows how wedge piece 36 is configured to be installed radially into an internal receptacle of carriage block 35.

FIGS. 16-21 show another embodiment of a holder using a ball joint type of mechanism. A traveler 60 has a rail passage 61 on one side and a ball socket 62 on the other side. A compressible ball 63 has a central opening or slot 64 for receiving an arm (i.e., strap segment) 65 of a retractor finger unit 66. Arm 65 terminates in a rake 67 and a sub-finger 68.

Lock levers 70 and 71 are mounted through respective pivot holes 72 and 73. Projecting lock tabs 74 and 75 variably extend through respective windows 76 and 77 into rail passage 61 and ball socket 62, respectively, by rotating lock levers 70 and 71. Thus, lever 70 is used to lock or release the holder for sliding along the rail of the sternal retractor.

In the released position of lever 71, ball 63 is allowed to rotate in any direction within ball socket 62 and arm 65 is allowed to slide within opening 64. When lever 71 is moved to its lock position, lock tab 75 prevents further rotation of ball 63 and compresses ball 63 so that arm 65 can no longer slide.

Opening 64 may include contour ridges 80 to maintain the alignment of arm 65. In addition, opening 64 may define an internal detent bump 81 for snapping into any one of a series of spaced openings 82 in arm 65.

What is claimed is:

1. Retraction apparatus for retracting tissue covering a mitral valve in surgical procedures, comprising:
   a holder configured to mount to a fixed rail; and
   a rake element comprising:
      a strap segment having a proximal end slidably received in a slot in the holder;
      a primary rake finger at a distal end of the strap segment configured to grasp and retract tissue at a surgical site; and
      a sub-finger extending perpendicularly via a bendable wing from a side of the primary rake finger adapted to retract adjacent tissue around the surgical site;
   wherein the primary rake finger, wing, and sub-finger are integrally formed of a malleable material; and
   wherein the holder is comprised of:
      a traveler member adapted to slide along the fixed rail;
      an articulating mechanism defining the slot and providing continuously adjustable sliding of the strap segment and rotation on an axis perpendicular to the fixed rail, so that the strap segment is adjustable with three degrees of freedom; and a tightener for clamping the articulating mechanism to lock the proximal end of the strap segment with the primary rake finger and the sub-finger extended to a desired location for retracting the tissue.

2. The retraction apparatus of claim 1 wherein the malleable material is comprised of biocompatible metal.

3. The retraction apparatus of claim 1 wherein the primary rake finger and the sub-finger each has a respective distal end comprising a hook-shaped plate to grasp the tissue.

4. The retraction apparatus of claim 1 wherein the primary rake finger, wing, sub-finger, and strap segment are integrally formed of a malleable material.

5. The retraction apparatus of claim 1 wherein the primary rake finger, wing, sub-finger, and strap segment are comprised of a continuous metal sheet.

6. The retraction apparatus of claim 1 wherein the fixed rail comprises a sternal retractor.

7. Retraction apparatus for surgical procedures, comprising:
   a rake element comprising:
      a strap segment;
      a primary rake finger at a distal end of the strap segment configured to grasp and retract tissue at a surgical site; and
      a sub-finger extending perpendicularly via a bendable wing from a side of the primary rake finger adapted to retract adjacent tissue around the surgical site; and
   a holder, configured to mount to a fixed rail, having a slot which slidably receives the proximal end of the strap segment, comprised of:
      a traveler member adapted to slide along the fixed rail;
      an articulating mechanism defining the slot and providing continuously adjustable sliding of the strap segment; and
      a tightener for clamping the articulating mechanism to lock the proximal end of the strap segment with the primary rake finger and the sub-finger extended to a desired location for retracting the tissue;
   wherein the articulating mechanism is comprised of a carriage block and a wedge piece having adjacent curved surfaces defining the slot, wherein the carriage block and wedge piece are mounted through an aperture in the traveler member, wherein the tightener is comprised of a knob with a threaded shaft, wherein the carriage block includes a threaded bore receiving the threaded shaft, and wherein tightening of the knob presses the strap segment against the wedge piece to lock the strap segment and to restrain the carriage block and wedge piece from rotating in the aperture;
   wherein the primary rake finger, wing, and sub-finger are integrally formed of a malleable material.

8. The retraction apparatus of claim 7 wherein tightening of the knob presses the wedge piece against the fixed rail to restrain the traveler member.

9. Retraction apparatus for surgical procedures, comprising:
   a rake element comprising:
      a strap segment;
      a primary rake finger at a distal end of the strap segment configured to grasp and retract tissue at a surgical site; and
      a sub-finger extending perpendicularly via a bendable wing from a side of the primary rake finger adapted to retract adjacent tissue around the surgical site; and
   a holder, configured to mount to a fixed rail, having a slot which slidably receives the proximal end of the strap segment, comprised of:
      a traveler member adapted to slide along the fixed rail;
      an articulating mechanism defining the slot and providing continuously adjustable sliding of the strap segment; and
      a tightener for clamping the articulating mechanism to lock the proximal end of the strap segment with the primary rake finger and the sub-finger extended to a desired location for retracting the tissue;
   wherein the traveler member includes a ball socket;
   wherein the articulating mechanism is comprised of a compressible ball in the ball socket with a central opening receiving the strap segment, and wherein the tightener is comprised of a lock lever with a projecting lock tab to selectably compress the ball to lock the strap segment.

10. The retraction apparatus of claim 9 wherein the traveler member further includes a second locking lever with a second projecting lock tab to selectably restrain the traveler member on the fixed rail.

* * * * *